United States Patent
Lu et al.

(10) Patent No.: US 9,317,023 B2
(45) Date of Patent: Apr. 19, 2016

(54) WIRE SORTING MACHINE AND METHOD OF SORTING WIRES

(71) Applicants: Tyco Electronics Corporation, Berwyn, PA (US); Shenzhen AMI Technology Co. Ltd., Shenzhen (CN)

(72) Inventors: Roberto Francisco-Yi Lu, Bellevue, WA (US); Qinglong Zeng, Shenzhen (CN); Charles David Fry, New Bloomfield, PA (US); Bicheng Chen, Harrisburg, PA (US)

(73) Assignees: Tyco Electronics Corporation, Berwyn, PA (US); Shenzhen AMI Technology Co. Ltd., Shenzhen (CN)

( * ) Notice: Subject to any disclaimer, the term of this patent is extended or adjusted under 35 U.S.C. 154(b) by 447 days.

(21) Appl. No.: 13/833,404

(22) Filed: Mar. 15, 2013

(65) Prior Publication Data
US 2014/0081464 A1  Mar. 20, 2014

Related U.S. Application Data

(60) Provisional application No. 61/703,356, filed on Sep. 20, 2012.

(51) Int. Cl.
*G05B 15/02* (2006.01)
*H01R 43/28* (2006.01)

(52) U.S. Cl.
CPC .............. *G05B 15/02* (2013.01); *H01R 43/28* (2013.01)

(58) Field of Classification Search
None
See application file for complete search history.

(56) References Cited

U.S. PATENT DOCUMENTS

| 5,709,025 A | 1/1998 | Wuyts |
| 6,370,769 B1 * | 4/2002 | Lilienthal, II ................... 29/861 |
| 2003/0196320 A1 * | 10/2003 | Ikeda et al. ..................... 29/749 |

FOREIGN PATENT DOCUMENTS

| DE | 31 12 205 A1 | 10/1982 |
| DE | 39 34 401 A1 | 4/1991 |
| DE | 43 01 043 C1 | 5/1994 |
| EP | 1 355 389 A2 | 10/2003 |

OTHER PUBLICATIONS

International Search Report, International Application No. PCT/US2013/059107, International Filing Date, Sep. 11, 2013.

* cited by examiner

*Primary Examiner* — Sean Shechtman
*Assistant Examiner* — Steven Garland (57) ABSTRACT

A wire sorting machine includes a frame and a fixture held by the frame. The fixture is configured to support a cable having a plurality of wires. A positioning system is supported by the frame. A guidance system is supported by the positioning system. The guidance system has a camera viewing the fixture that is movable relative to the fixture. A wire manipulator is supported by the positioning system and is moved by the positioning system relative to the fixture. The wire manipulator is configured to engage the wires of the cable to position the wires relative to the fixture. A controller communicates with the positioning system and the guidance system. The controller operates the positing system to control a position of the wire manipulator relative to the fixture based on an image obtained by the camera.

20 Claims, 5 Drawing Sheets

WIRE SORTING MACHINE AND METHOD OF SORTING WIRES

CROSS REFERENCE TO RELATED APPLICATIONS

This application claims the benefit of U.S. Provisional Application No. 61/703,356 filed Sep. 20, 2012, the subject matter of which is herein incorporated by reference in its entirety.

BACKGROUND OF THE INVENTION

The subject matter herein relates generally to wire sorting machines and methods of sorting wires.

Many electrical components are mounted to ends of cables. The cables have individual wires that are terminated to the various components of the electrical component. For example, the wires may be soldered to circuit boards or terminated to contacts or terminals. Assembly of the electrical components and connection of the electrical components to the cables is time consuming. Typically, the wires are positioned manually, such as by an operator lacing the wires into a wire organizer for holding the wires in position for terminating to the circuit board or contacts. Such manual lacing is time consuming.

There is a need for a cost effective automated process of sorting wires of a cable without human operator intervention.

BRIEF DESCRIPTION OF THE INVENTION

In one embodiment, a wire sorting machine is provided including a frame and a fixture held by the frame. The fixture is configured to support a cable having a plurality of wires. A positioning system is supported by the frame. A guidance system is supported by the positioning system. The guidance system has a camera viewing the fixture that is movable relative to the fixture. A wire manipulator is supported by the positioning system and is moved by the positioning system relative to the fixture. The wire manipulator is configured to engage the wires of the cable to position the wires relative to the fixture. A controller communicates with the positioning system and the guidance system. The controller operates the positing system to control a position of the wire manipulator relative to the fixture based on an image obtained by the camera.

Optionally, the camera may differentiate the wires based on a color of the wires. The controller may operate the positioning system to control a position of the wire manipulator based on the color of the wire. The controller may develop a motion profile for the positioning system to move the wire manipulator. The motion profile may have movements for sequentially positioning more than one wire.

Optionally, the fixture may include wire holders and the wire manipulator moves the wires into position relative to the wire holder. The wire manipulator may grip individual wires to manipulate the wires into position. The camera may image the position of the wires after at least one wire is positioned by the wire manipulator. The controller may update operation of the positioning system based on the new image of the wires. The positioning system may include an X positioner, a Y positioner, and a Z positioner to control a position of the wire manipulator in 3D space. The positioning system may include an angular positioner to control an angle of the wire manipulator relative to the fixture. The guidance system may include an optical component affecting an image of the wires taken by the camera.

Optionally, the guidance system may include an optical component having an illumination source emitting light at different wavelengths on the wires. The controller may differentiate the wires based on the light emitted by the illumination source. The controller may operate a wire recognition algorithm determining a shape and position of each wire. The controller may determine a motion profile for moving the wire manipulator based on the determined shape and positioning.

In another embodiment, a method of sorting wires of a cable is provided including holding the cable on a fixture, capturing an image of the wires using a camera, developing a motion profile based on the arrangement of the wires from the image using a wire recognition algorithm of a controller, and moving a wire manipulator to change positions of the wires relative to the fixture based on the motion profile.

DETAILED DESCRIPTION OF THE INVENTION

Figure 1:
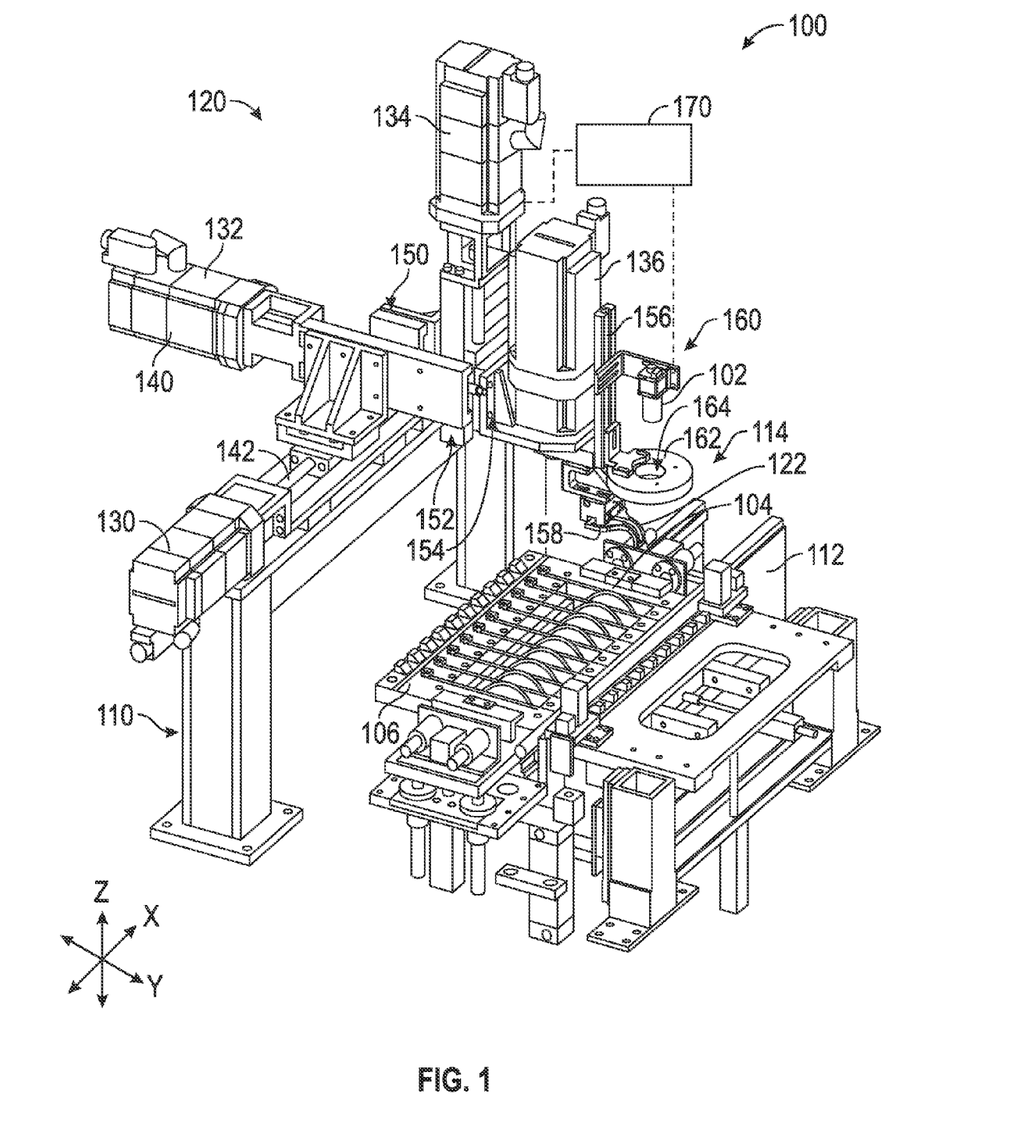
FIG. 1 illustrates a wire sorting machine formed in accordance with an exemplary embodiment.

FIG. 1 illustrates a wire sorting machine 100 formed in accordance with an exemplary embodiment. The wire sorting machine 100 is used for separating individual wires of a cable and positioning the wires in proper position, such as for attachment to a circuit board or for attachment to a contact or terminal. The wire sorting machine 100 automatically sorts the wires using an automated process.

The wire sorting machine 100 provides vision guidance using a camera 102 to collect images and data relating to the wires and dynamically change parameters and control of the components of the wire sorting machine 100. Each cable presented to the wire sorting machine 100 may have a different layout of the wires (e.g. the wires exit the cable in a random orientation) and the wire sorting machine 100 identifies specific wires and properly positions the wire, such as for soldering to a circuit board. In an exemplary embodiment, the wires are color coded and each wire requires a predetermined position for termination to the circuit board. Such a layout may be generally defined as a footprint. The wire sorting machine 100 uses images from the camera 102 to identify characteristics of the wires, such as the layout, shape, positional data, color and the like, to distinguish which wire is which and to develop a motion profile for properly placing each of the wires. For example, the wire sorting machine 100 may determine which wires are overlapping wires and which wires are overlapped wires. The wire sorting machine 100 may first move the overlapping wires into position, thus exposing and allowing the overlapped wires to be accessible for moving such wires. The parameters and control of the wire sorting machine 100 may be based on geometrical characteristic data obtained based upon the image captured by the camera 102.

In the illustrated embodiment, the wire sorting machine 100 processes a plurality of cables 104 (each having individual wires). The cables 104 are held on a fixture 106. Any number of cables 104 may be held by the fixture 106. Alternatively, the cables 104 may be individually presented to the wire sorting machine 100 rather than being presented as a batch as part of the fixture 106. In an exemplary embodiment, both ends of the cables 104 may be processed by the wire sorting machine 100 to sort the wires extending from both ends of the cables 104. Alternatively, the wires extending from only one end of the cables 104 may be sorted. In other alternative embodiments, the system may include two or more wire sorting machines 100 for sorting different cables 104 or different ends of the cables 104 held by the same fixture 106. The control of the wire sorting machines 100 may be synchronized or managed to ensure the components do not impact one another.

The wire sorting machine 100 includes a frame 110 that supports the various components of the wire sorting machine 100. The frame 110 may be stationary. The frame 110 may be part of a larger machine, such as positioned at a station before or after other stations. In an exemplary embodiment, the frame 110 includes a track 112. The fixture 106 may be conveyed along the track 112. Optionally, once the fixture 106 is positioned in a working zone 114 of the wire sorting machine 100, the fixture 106 may be held in place and restricted from moving along the track 112.

The wire sorting machine 100 includes a positioning system 120 supported by the frame 110. The positioning system 120 is used to position the camera 102 relative to the fixture 106 during operation of the wire sorting machine 100. The positioning system 120 is used to position a wire manipulator 122 relative to the fixture 106 during operation of the wire sorting machine 100. The wire manipulator 122 is used to physically move the wires. The wire manipulator 122 is movable in three dimensions to move the wires according to a particular motion profile determined by the wire sorting machine 100 based on the particular arrangement of the wires. In the illustrated embodiment, the positioning system 120 is a Cartesian motion robot with rotary axis. Other types of systems may be used in other embodiments, such as a selective compliance assembly robot arm (SCARA) or other robotic motion system.

In an exemplary embodiment, the positioning system 120 includes an X positioner 130, a Y positioner 132, a Z positioner 134 and at least one angular positioner 136 to allow movement of components of the wire sorting machine 100 in three dimensional space. A coordinate system is illustrated in FIG. 1 showing mutually perpendicular X, Y and Z axes. The X positioner 130 allows movement along the X axis. Optionally, the X axis may be parallel to the track 112. The Y positioner 130 allows movement along the Y axis. The Z positioner 130 allows movement along the Z axis. The angular positioner 136 allows movement along at least one angular path. In an exemplary embodiment, the positioners 130, 132, 134, 136 include motors 140 that drive shafts 142. The motors 140 may be electric motors, pneumatic motors, or other types of motors. The motors 140 may be servo motors.

In an exemplary embodiment, the X positioner 130 includes a pod 150. The Y positioner 132 may be coupled to the pod 150, such as by a clamp on the pod 150. The Y positioner 132 may be movable in the X direction as the X positioner 130 is operated. The Y positioner 132 includes a pod 152. The Z positioner 134 may be coupled to the pod 152, such as by a clamp on the pod 152. The Z positioner 134 may be movable in the X direction as the X positioner 130 is operated and in the Y direction as the Y positioner 132 is operated. The Z positioner 134 includes a pod 154. The angular positioner 136 may be coupled to the pod 154, such as by a clamp on the pod 154. The angular positioner 136 may be movable in the X direction as the X positioner 130 is operated, in the Y direction as the Y positioner 132 is operated, and in the Z direction as the Z positioner 134 is operated. Other configurations are possible in alternative embodiments.

The camera 102 may be coupled to the angular positioner 136. For example, the camera 102 may be coupled to the angular positioner 136 using a bracket 156. Alternatively, the camera 102 may be coupled to the pod 154. The camera 102 may be coupled to other components in alternative embodiments while being movable with the positioning system 120. The wire manipulator 122 may be coupled to an arm 158 of the angular positioner 136. The wire manipulator 122 is movable with the positioners 130, 132, 134, 136. Optionally, multiple cameras 102 may be provided that view the wire sorting area at different angles. Alternatively, a stereoscope may be used.

The wire sorting machine 100 includes a guidance system 160 that provides visual guidance for guiding movement of the wires. The camera 102 forms part of the guidance system 160. The camera 102 is aimed at the work zone 114 and takes images of the wire manipulator 122 and/or the wires. Optionally, the camera 102 may take continuous images and the wire sorting machine 100 may continuously update operation based on such images. Alternatively, the camera 102 may take images at predetermined times, such as at each new cable end location prior to sorting the wires, at various stages of the wire sorting (e.g. after each wire is positioned), at predetermined times intervals (e.g. 1 image per second), and the like.

In an exemplary embodiment, the guidance system 160 includes an optical component 162 for controlling optical characteristics of the wire sorting machine 100. For example, the optical component 162 may include an illumination source for illuminating the work zone 114, wire manipulator 122 and/or the wires. The illumination source may emit lights at different wavelengths on the wires to facilitate identification of the corresponding wires. The different light wavelengths may be used to distinguish different color wires from one another. The lights may provide shadows to identify overlapping of certain wires.

The optical component 162 may include an opening 164 therethrough. The imaging of the camera 102 may be focused through the opening 164. The optical component 162 limits the viewing area to limit the data processed by the wire sorting machine 100 for faster operation of the wire sorting machine 100. For example, portions of the wires outside of the visible boundary defined by the opening 164 may be hidden from view, and therefore not processed by the wire sorting machine 100 in determine the motion profile.

The wire sorting machine 100 includes a controller 170 that controls operation of the wire sorting machine 100. The controller 170 communicates with the positioning system 120 and the guidance system 160. For example, the images generated by the camera 102 are processed by the controller 170. The controller 170 includes a motion planning and process parameter calculation algorithm. The controller 170 includes a wire sorting algorithm that formulates a motion profile for the wire sorting machine 100. The wire sorting algorithm is based on the images provided by the camera 102. The wire sorting algorithm identifies each individual wire, including the shape and location of the wire and identifies the proper final position of the wire based on the particular wire identified. The wire sorting algorithm determines a plan for sorting the wires. The wire sorting algorithm calculates a series of movements for the positioning system 120 to efficiently move one or more of the wires. The wire sorting algorithm may determine an efficient motion profile for sorting the wires. For example, the wire sorting algorithm may determine a sorting order for the wires based on the observed positions of the wires. Because the wires randomly exit the cable (e.g. different cables may have different arrangements of wires), different color wires may be on top and different color wires may be on bottom of different cables. For one cable, a red wire may be sorted first but for another cable, the red wire may be sorted second, third, last, etc. The motion profile is specific to the particular cable, is based upon the in situ orientation of the wires and is automatically generated and updated by the controller on the fly.

In an exemplary embodiment, the illumination source emits the lights onto the wires to assist the wire sorting algorithm in identifying the individual wires. The identification process may be based on the intensity of the wire in the image. For example, different color wires have different intensity levels in the image, which aids the wire sorting algorithm in identifying the wires.

The controller 170 controls the X, Y, Z and angular position of the wire manipulator 122 during operation of the wire sorting machine 100. The controller 170 controls the X, Y, Z and angular position of the camera 102 during operation of the wire sorting machine 100. The controller 170 uses the wire sorting algorithm to develop a motion profile for sorting each of the wires of the cables 104. In operation, the controller 170 positions the camera 102 and wire manipulator 122 at a series of stations, where an end of a cable 104 is provided at each station. At each station, the camera 102 images the arrangement of the wires and the controller 170 determines a series of steps to efficiently sort the wires based on the particular arrangement of the wires. The wire sorting algorithm develops a motion profile, which includes a series of movements of the wire manipulator 122, for sorting the individual wires. Once all the wires are sorted, the controller 170 moves the camera 102 and wire manipulator 122 to the next station and sorts the next set of wires. The controller 170 may plan a different motion profile at each station because the arrangement of the wires at each station may be different.

Figure 2:
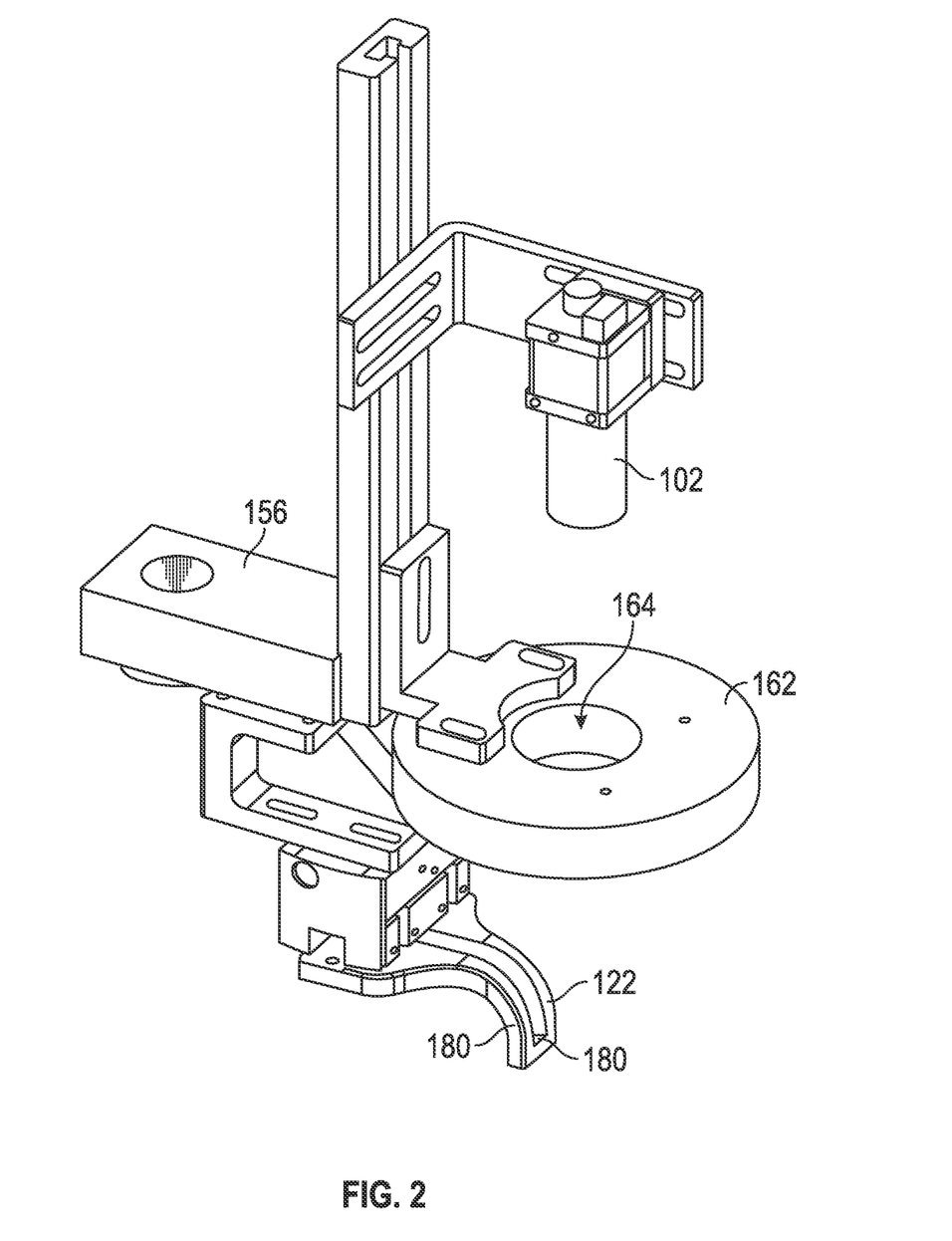
FIG. 2 illustrates a camera and wire manipulator for the wire sorting machine.

FIG. 2 illustrates the camera 102 and wire manipulator 122 mounted to the bracket 156. The camera 102 provides visual feedback for control of the machine. The position of the camera 102 and optical component 162 relative to the bracket 156 may be adjustable. The positions may be manually adjustable or automatically adjustable. The camera 102 is positioned directly above the opening 164 and aimed through the opening 164. The opening 164 defines the field of view for the images taken by the camera 102. The wire manipulator 122 is positioned below the optical component 162. The wire manipulator 122 may be viewable by the camera 102 through the opening 164. Alternatively, if not viewable, the position of the wire manipulator 122 relative to the image may be known and used by the controller 170 (shown in FIG. 1) to control movements of the wire manipulator 122.

The wire manipulator 122 is configured to manipulate the wires of the cables 104 (shown in FIG. 1). In an exemplary embodiment, the wire manipulator 122 is configured to grasp or pinch the wires to move the wires with the wire manipulator 122. For example, the wire manipulator 122 may include one or more fingers 180 that hold the wire to move the wire during operation of the wire sorting machine 100 (shown in FIG. 1). In alternative embodiments, the wire manipulator 122 may move the wires by other means, such as by pushing the wires or pulling the wires in a certain direction as the wire manipulator is moved.

Optionally, the fixture may include a flattening plate in the area of the wires. The flattening plate limits the position of the wires generally in a plane for manipulation by the wire manipulator. The wire manipulator 122 may capture the wires between the tip of the wire manipulator 122 and the flattening plate for positioning the wires.

Figure 3:
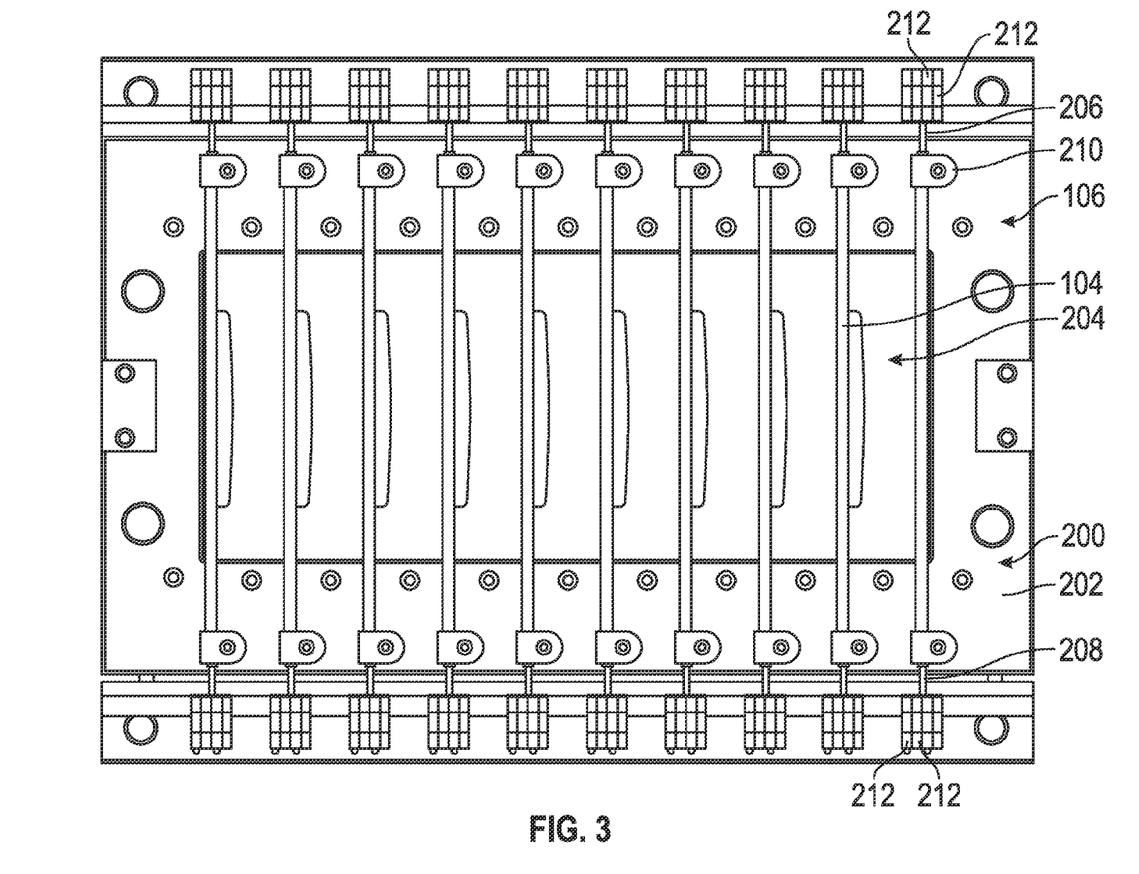
FIG. 3 is a top view of a fixture of the wire sorting machine with cables loaded therein.

FIG. 3 is a top view of the fixture 106 with the cables 104 loaded therein. The fixture 106 may hold any number of cables 104. The fixture 106 includes a plate 200 having an upper surface 202. The cables 104 extend along and are held against the upper surface 202. In an exemplary embodiment, the plate 200 includes a cavity 204 with an opening through the upper surface 202. Excess lengths of the cables 104 may be coiled or contained in the cavity 204 with ends 206, 208 of the cables 104 positioned along the upper surface 202. In an exemplary embodiment, both ends 206, 208 are positioned along the upper surface 202 for sorting of the wires at both ends 206, 208. Alternatively, the wires of only one end 206 may be sorted.

The fixture 106 includes cable clamps 210 to hold the cables 104 in place along the upper surface 202. The cable clamps 210 hold the ends 206, 208 in place such that the wires, extending from the ends 206, may be sorted. The cable clamps 210 may be pneumatically operated. The cable clamps 210 may be spring biased. The cables 104 may be positioned relative to the cable clamps 210 by an automated process, or alternatively may be manually positioned.

The fixture 106 includes a plurality of wire holders 212 to hold the individual wires of each cable 104 in place along the upper surface 202. Optionally, the upper surface 202 may have cradles that receive the wires and control the relative positions of the wires. The wire holder 212 may hold the wires in the cradles. The wire holders 212 hold the ends of the wires once the wires are sorted. In operation, the wire sorting machine 100 (shown in FIG. 1) places the appropriate wire at the corresponding wire holder 212 and the wire holder 212 then holds the end of the wire in place, such as for soldering to a circuit board, for terminating a contact or terminal thereto, or for other processing, such as plating, coating, or other processing. Optionally, the wire holders 212 may be spring biased. In an alternative embodiment, a single wire holder 212 may hold all of the wires of a corresponding cable or all of the wires from multiple cables.

Figure 4:
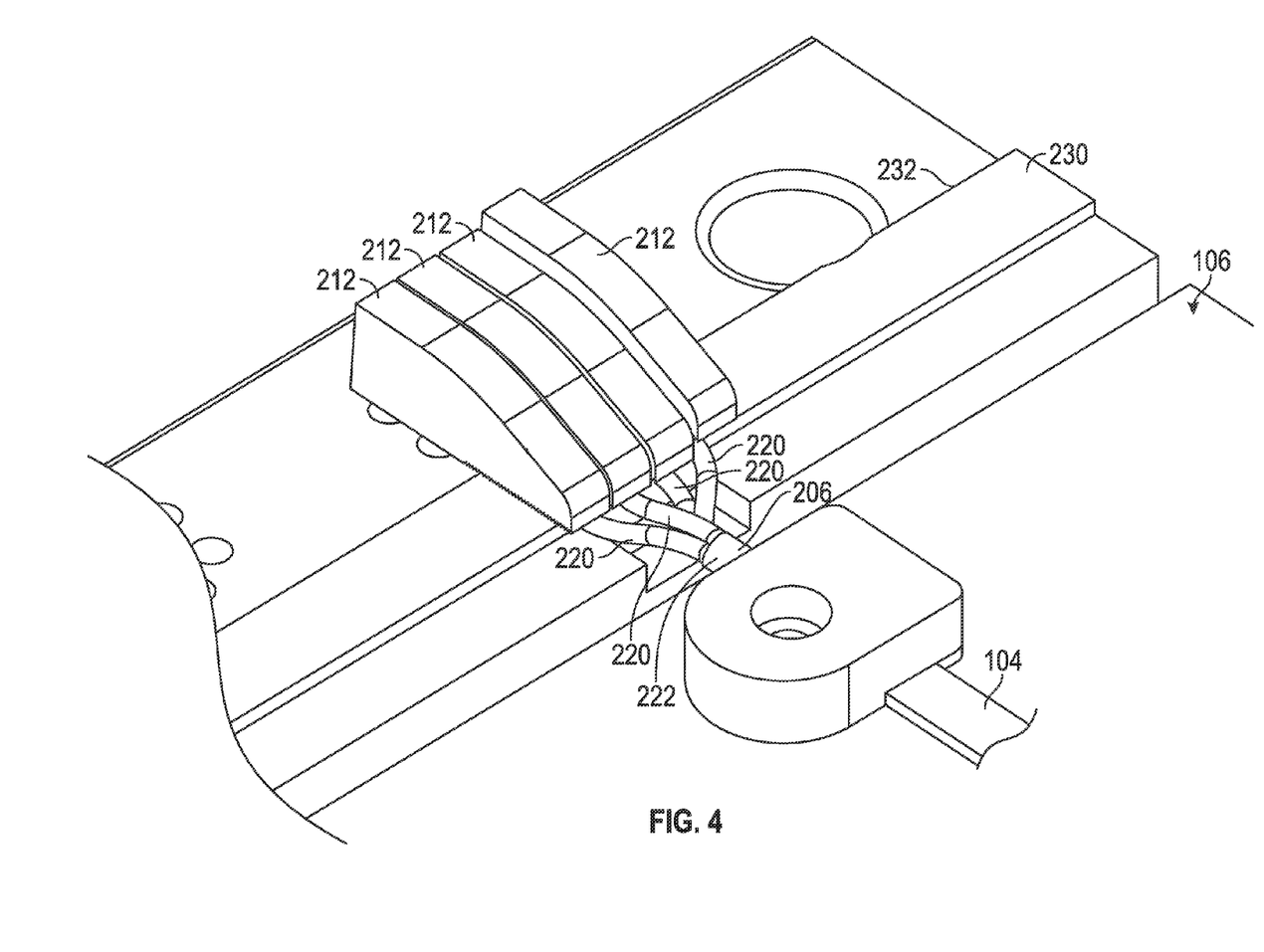
FIG. 4 is an enlarged view of a portion of the fixture showing wires held by wire holders of the fixture.

FIG. 4 is an enlarged view of a portion of the fixture 106 showing wires 220 held by the wire holders 212. The wires 212 extend from the end 206 of the cable 104 beyond a jacket 222 of the cable 104. In an exemplary embodiment, the wires 220 need to be positioned in a particular arrangement (e.g. each wire 220 needs to be at a particular location or position), such as for soldering to a circuit board. The arrangement of the wires 220 exiting the jacket 222 may be random and may vary from cable to cable. The wire sorting machine 100 (shown in FIG. 1) is able to visually identify each individual wire 220, such as by using color recognition of the wires 220, to properly position the wires 220 at the correct location. The wire sorting machine 100 positions the wires 220 under the wire holders 212 and the wire holders 212 hold the wires 220 in position.

In an exemplary embodiment, the fixture 106 includes a step 230. The wires 220 are held between the step 230 and the wire holders 212. The wires 220 may extend beyond an edge 232 of the step 230, where the wires 220 may be terminated to the circuit board. For example, the circuit board may be positioned in the area beyond the edge 232, and the wires 220, while being held by the wire holders 212, may be soldered to the circuit board.

Figure 5:
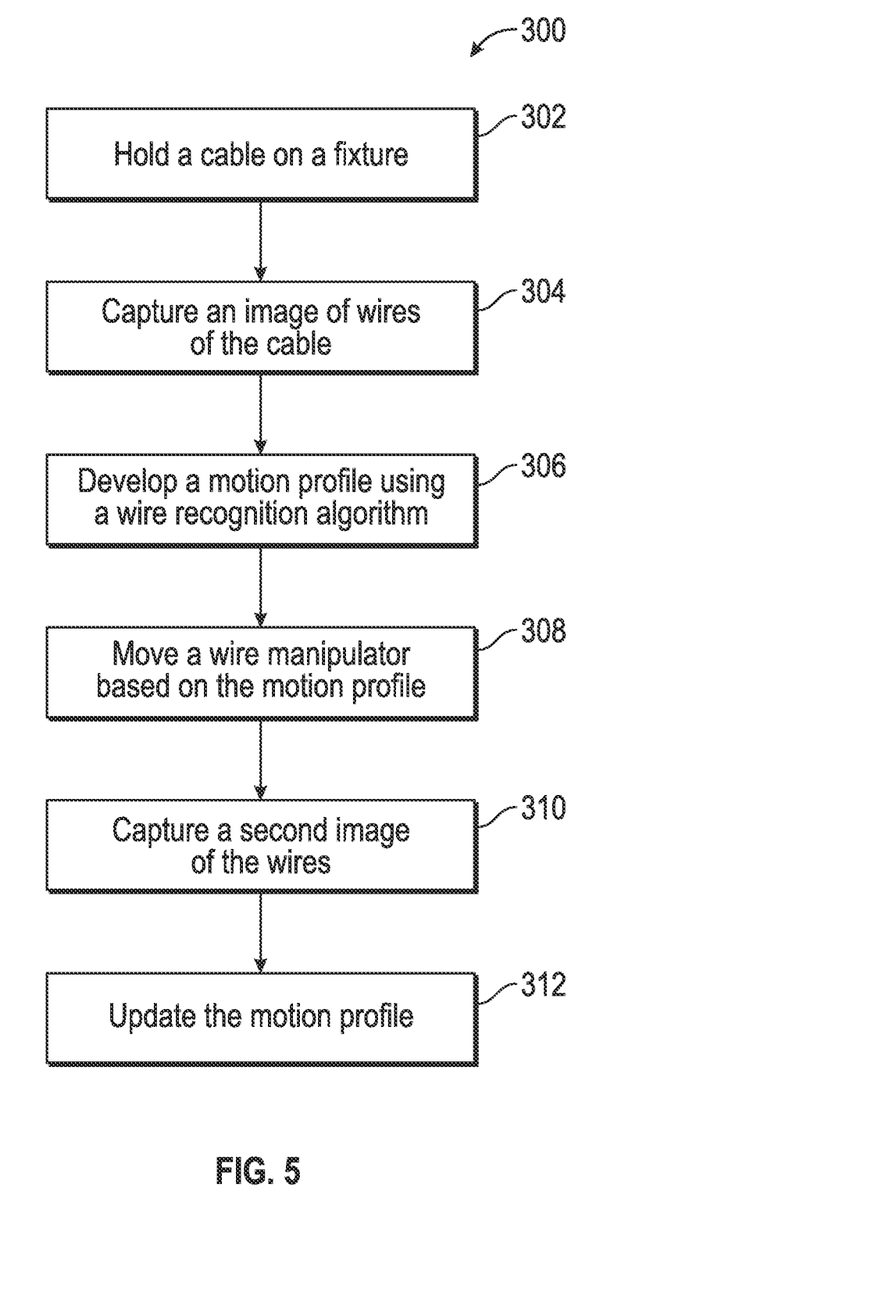
FIG. 5 illustrates a method of sorting wires of a cable.

FIG. 5 illustrates a method 300 of sorting wires of a cable. At 302, the method includes holding a cable on a fixture. For example, the cable may be held by cable clamps. Optionally, both ends of the cable may be held on the fixture. The cable is held such that individual wires of the cable extend from an end of a jacket of the cable for sorting.

At 304, the method includes capturing an image of a cable. The image may be captured by a camera aimed at the end of the cable. The camera views the arrangement of the wires exposed at the end of the cable. The camera may capture more than one image. Multiple cameras may be provided to view different portions or angles of the wires and cable. Optionally, the image zone may be illuminated by an illumination source. The wires may be illuminated by lights of different wavelengths. The wires may be different color wires and may be affected differently by the different wavelength lights.

At 306, the method includes developing a motion profile for the wire sorting machine. The motion profile controls movement of a wire manipulator that moves the wires. The motion profile includes a set of instructions executable by a computer to control operation of the wire sorting machine. In an exemplary embodiment, the wire sorting machine includes a controller for controlling operation of the wire sorting machine. The controller includes a wire recognition algorithm that determines the arrangement of the wires based on the captured image. The wire recognition algorithm distinguishes between the different wires, such as based on the color of the wires. For example, when the wires are illuminated by lights of different wavelength, the controller may determine which wire is which using recognition software and the wire recognition algorithm. The controller determines the shape and arrangement of the wires. The controller determines an overlapping scheme to identify which wires are overlapping wires and which wires are overlapped wires. The controller determines which wire is on top, and the controller may determine that such wire should be moved first, however other wires may be moved first in other situations. Data from the image is used to generate the motion profile and the wire sorting machine is operated according to the motion profile. Optionally, the motion profile may be updated and corrected for after one or more of the wires are moved.

At 308, the method includes moving the wire manipulator based on the motion profile. For example, the wire sorting machine may include positioners that move the wire manipulator relative to the fixture. The wire manipulator may grasp or otherwise engage the wire to move the wire to a proper location with respect to the fixture. For example, the wires initially exit the cable with the wires being twisted, nested, intertwined and/or overlapping one another. The wires are positioned by the wire manipulator in a predefined arrangement, such as parallel and spaced apart in a coplanar manner. The wire manipulator moves the wires one at a time to the proper positions.

At 310, in some embodiments, the method may include capturing a second image of the wires. At 312, the motion profile may be updated, such as based on the second image. The second image may be captured after one or more wires have been moved. Updating of the motion profile ensures accurate placement of the wires.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. Dimensions, types of materials, orientations of the various components, and the number and positions of the various components described herein are intended to define parameters of certain embodiments, and are by no means limiting and are merely exemplary embodiments. Many other embodiments and modifications within the spirit and scope of the claims will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. §112, sixth paragraph, unless and until such claim limitations expressly use the phrase "means for" followed by a statement of function void of further structure.

What is claimed is:

1. A wire sorting machine comprising:
   a frame;
   a fixture held by the frame, the fixture being configured to support a cable having a plurality of wires;
   a positioning system supported by the frame;
   a guidance system supported by the positioning system, the guidance system having a movable camera viewing the fixture, the camera being movable relative to the fixture;
   a movable wire manipulator supported by the positioning system and moved by the positioning system relative to the fixture and the cable, the wire manipulator sequentially gripping individual wires of the cable to individually position the wires relative to the fixture; and
   a controller communicating with the positioning system and the guidance system, the controller operating the positioning system and controlling a position of the wire manipulator relative to the fixture based on an image obtained by the camera.

2. The wire sorting machine of claim 1, wherein the camera is configured to differentiate the wires based on a color of the wires, the controller operating the positioning system to control a position of the wire manipulator based on the color of the wire.

3. The wire sorting machine of claim 1, wherein the controller develops a motion profile for the positioning system to move the wire manipulator.

4. The wire sorting machine of claim 1, wherein the controller develops a motion profile for the positioning system to move the wire manipulator, the motion profile having movements for sequentially positioning more than one wire.

5. The wire sorting machine of claim 1, wherein the fixture includes wire holders, the wire manipulator moving the wires into position relative to the wire holder, the wire holders holding the wires.

6. The wire sorting machine of claim 1, wherein the wires are layered above the fixture, the wire manipulator grips an outermost one of the layered wires to manipulate such wire into position.

7. The wire sorting machine of claim 1, wherein the camera images the position of the wires after at least one wire is positioned by the wire manipulator.

8. The wire sorting machine of claim 7, wherein the controller updates operation of the positioning system based on the new image of the wires.

9. The wire sorting machine of claim 1, wherein the positioning system includes an X positioner, a Y positioner, and a Z positioner to control a position of the wire manipulator in 3D space.

10. The wire sorting machine of claim 9, wherein the positioning system includes an angular positioner to control an angle of the wire manipulator relative to the fixture.

11. The wire sorting machine of claim 1, wherein the guidance system includes an optical component affecting an image of the wires taken by the camera.

12. The wire sorting machine of claim 1, wherein the guidance system includes an optical component, the optical component having an illumination source emitting light at different wavelengths on the wires, the controller differentiating the wires based on the light emitted by the illumination source.

13. The wire sorting machine of claim 1, wherein the controller operates a wire recognition algorithm determining a shape and position of each wire, the controller determining a motion profile for moving the wire manipulator based on the determined shape and positioning.

14. A method of sorting wires of a cable comprising:
holding the cable on a fixture;
capturing an image of the wires using a camera;
developing a motion profile based on the arrangement of the wires from the image using a wire recognition algorithm of a controller;
sequentially gripping the wires one at a time based on the motion profile using a movable wire manipulator; and
moving the wire manipulator relative to the cable and the fixture to change positions of the wires relative to the fixture based on the motion profile.

15. The method of claim 14, wherein said developing a motion profile is based on which wire is on top.

16. The method of claim 14, wherein said developing a motion profile includes determining an overlapping scheme to identify which wires overlap other wires, said moving a wire manipulator comprises moving the wire manipulator to change positions of the overlapping wires prior to overlapped wires.

17. The method of claim 14, wherein said developing a motion profile comprises developing a motion profile based on colors of the wires.

18. The method of claim 14, wherein said capturing an image comprises illuminating the wires with light of different wavelengths, said developing a motion profile comprises distinguishing the wires based on the illumination effects of the image.

19. The method of claim 14, wherein said moving the wire manipulator to change positions of the wires comprises sequentially picking up the wires using the wire manipulator and placing the wires in position relative to the fixture.

20. The method of claim 14, further comprising capturing a second image of the wires using the camera after at least one of the wires is put in position by the wire manipulator and updating the motion profile based on the second image.

* * * * *